US008178745B2

(12) United States Patent
Bader

(10) Patent No.: US 8,178,745 B2
(45) Date of Patent: May 15, 2012

(54) PLASTER WHICH RELEASES ACTIVE COMPOUND

(76) Inventor: Augustinus Bader, Klinga (DE)

(*) Notice: Subject to any disclaimer, the term of this patent is extended or adjusted under 35 U.S.C. 154(b) by 791 days.

(21) Appl. No.: 12/168,938

(22) Filed: Jul. 8, 2008

(65) Prior Publication Data

US 2009/0018481 A1 Jan. 15, 2009

(30) Foreign Application Priority Data

Jul. 9, 2007 (EP) .................................. 07013361

(51) Int. Cl.
*A61F 13/00* (2006.01)
(52) U.S. Cl. ............................................. 602/42; 602/48
(58) Field of Classification Search ............... 602/41–54
See application file for complete search history.

(56) References Cited

U.S. PATENT DOCUMENTS

| 4,360,021 A * | 11/1982 | Stima .......................... 604/365 |
| 4,990,144 A * | 2/1991 | Blott ........................... 604/304 |
| 5,505,720 A * | 4/1996 | Walters et al. ................ 604/378 |
| 2008/0135441 A1 * | 6/2008 | Meliniotis et al. ............ 206/531 |

FOREIGN PATENT DOCUMENTS

| WO | 96/40749 | 12/1996 |
| WO | 96/40772 | 12/1996 |
| WO | 01/02017 | 1/2001 |
| WO | 01/38342 | 5/2001 |
| WO | 01/91780 | 12/2001 |
| WO | 02/49673 | 6/2002 |
| WO | 03/101361 | 12/2003 |
| WO | 2004/001023 | 12/2003 |
| WO | 2004/100997 | 11/2004 |
| WO | 2004/101600 | 11/2004 |
| WO | 2004/101606 | 11/2004 |
| WO | 2004/101611 | 11/2004 |
| WO | 2005/063965 | 7/2005 |
| WO | 2005/070450 | 8/2005 |
| WO | 2006/050959 | 5/2006 |
| WO | 2006/109325 | 10/2006 |

OTHER PUBLICATIONS

American J. Pathol. 2003, 163, 993. Haroon et al. (To Follow).
Kidney International, 2006. Brines and Cerami. (To Follow).

* cited by examiner

*Primary Examiner* — Michael A. Brown
(74) *Attorney, Agent, or Firm* — Davis & Bujold, P.L.L.C.

(57) ABSTRACT

The invention relates to a medical plaster which is able to supply damaged skin and open wounds with an active compound which helps to accelerate wound healing and allows it to proceed better. The plaster has novel design features which enable, in particular, protein- or peptide-containing medicaments, such as, for example, erythropoietin (EPO), to exert their wound-healing or wound-healing-promoting action by release of the active compound from the plaster without being significantly deactivated or metabolized in the process by substances occurring in the wound secretion.

40 Claims, 4 Drawing Sheets

PLASTER WHICH RELEASES ACTIVE COMPOUND

TECHNICAL AREA OF THE INVENTION

The invention relates to a medical plaster which is able to supply normal and damaged skin or mucous membrane, in particular open wounds, with one or more active compounds which help to accelerate and enhance regeneration of the skin or wound healing. The system can furthermore also be used to supply active compounds for the entire organism, where the dosage is not achieved as usual hitherto via concentration changes of the active compound.

The plaster has novel design features which enable, in particular, protein- or peptide-containing medicaments, besides conventional chemical substances, such as, for example, painkillers and nicotine, to exert their regenerative, in particular wound-healing or wound-healing-promoting action by release from the plaster without being significantly deactivated or metabolized by substances occurring in the wound secretion.

In addition, the plaster can be constructed in such a way that an active compound can be released uniformly to the wound or skin over an extended period, tailored individually to a particular patient, without the plaster having to be changed.

The plasters according to the invention are particularly suitable for the release of proteins as active compound with a relatively short half life, for example erythropoietin (EPO) in all its known variants and forms. In the case of EPO, its tissue-protecting or regenerative applications are of interest while avoiding the problem of administration of erythropoietin with its haemopoiesis-promoting action, which is undesired here.

TECHNICAL BACKGROUND OF THE INVENTION

Wound healing, for example of damaged skin or mucous membrane, usually proceeds in three phases: the inflammation phase, the proliferation phase and the reconstruction/remodelling phase. In the case of a fresh wound or skin injury which is to be treated, inflammatory processes, which encompass, in particular, the ingress of diverse inflammation factors (such as, for example, fibronectin) and cells of various types, such as, for example, monocytes, phagocytes, polymorphic cells and macrophages, take place within the first 24 hours, ultimately resulting in the formation of a fibrin matrix and vascular endothelial cells. Besides the said factors and cells, the wound secretion forming at the same time also contains cell detritus and a number of proteolytic enzymes as well as bacteria which have entered the wound and contain substances acting in this respect.

The proteolytic enzymes, some of which are highly active, are the reason why wound-healing-promoting, protein- or peptide-containing medicaments applied to the wound are often relatively or totally ineffective since the protein or polypeptide in question is deactivated, cleaved and degraded by said enzymes owing to its chemical and biological nature before it is able to develop an adequate pharmacological efficacy. The problem is additionally exacerbated by infection of the wound with bacteria or the ingress of cell debris. In all these processes, the respective half life of biodegradation of the medicament protein in question under the given physiological conditions plays a crucial role in the question of whether the said protein has adequate or adequately long efficacy in the case of damage to the skin, mucous membrane and the like if it is not administered systemically, such as, for example, subcutaneously or intravenously, but instead by application to the wound, i.e. topically.

For this reason, proteins and polypeptides which are particularly sensitive to enzymatic processes have hitherto not been employed successfully or not sufficiently successfully for topical application to skin wounds, even if it was attempted to introduce a physical barrier between the active compound and the wound and to maintain this for as long as possible, for example by means of corresponding porous membranes which only allow molecules smaller than 50,000 daltons to pass through. However, most proteolytic enzymes have a size larger than 100,000 daltons, which prevents them from migrating into the active-compound depot above the wound. Even with this measure, however, the effective half lifes of protein active compounds are very short since they are cleaved rapidly by proteolytic enzymes in the wound secretion forming on entry into the wound and are generally thereby rendered pharmacologically ineffective.

Another possibility for countering premature degradation of the active-compound protein is occasionally seen in the provision of slow-release formulations, in which the active compound is incorporated into a biodegradable polymer material, from which it is released in accordance with the kinetics of degradation of the polymer. However, these kinetics often do not correspond to the kinetics of degradation of the active compound after release into the wound.

Not least for this reason, pharmaceutical proteins are generally administered systemically, enabling their half life to be significantly extended and also transporting them more rapidly to the sites in the body where they are intended to develop their therapeutic efficacy. In this administration method, however, the doses of the protein-containing active compound must be sufficiently high in order to achieve the desired therapeutic effect, which often inevitably results in undesired side reactions.

In the case of therapeutic treatment of skin injuries, systemic administration of an active compound appears, in addition, less appropriate in principle since the healing effect of the medicament is actually only necessary locally. There is thus a general problem if protein-containing active compounds are to be employed for the treatment of skin injuries and open flesh and skin wounds.

Protein active compounds for use in injuries of this type, as can occur in the case of violent mechanical impacts and irritation and in burns and scalds, are known in principle. The use of growth factors, such as, for example, EGF, TGF beta, GCSF, GM-CSF, HGH, CNTF, EPO or TPO, in the healing of such conditions has thus recently been discussed.

In particular, importance is increasingly being attached to the non-haematopoietic action of erythropoietin (EPO) in connection, for example, with the stimulated formation and regeneration of endothelial and tissue cells, such as connective tissue, muscle tissue, epithelial tissue and nerve tissue, which has not been known for very long.

Thus, WO 2004/001023 describes, inter alia, the use of EPO and TPO for stimulating vascular re-formation and tissue regeneration and improving wound healing, for example after operations or injuries.

WO 2005/063965 teaches the use of EPO for the targeted structurally controlled regeneration of traumatised tissue, where topical or transdermal administration of the active compound is also proposed, where not only is endothelial cell growth stimulated, but also parenchymal regeneration and the formation of the wall structures are promoted, so that coordinated three-dimensional growth for the build-up of a functional tissue, organ or parts thereof takes place.

WO 2005/070450 describes the use of EPO in the regeneration of vessels and tissue with a weekly dose of less than 90 IU/kg of body weight for the area of wound treatment also. Although possible topical application is in principle mentioned here, it is nevertheless emphasized that systemic administration is preferred.

Haroon et al. (American J. Pathol. 2003, 163, 993) discuss the novel role of EPO in wound-healing processes induced by fibrin.

In a review article, Brines and Cerami (Kidney International, 2006) discuss the role of EPO in the protection of tissue.

Erythropoietin, EPO derivatives, such as, for example, pegylated or dimerized EPO (for example WO 02/49673 or WO 01/02017), and presumably also correspondingly active synthetic EPO peptide mimetics (as known, for example, from WO 96/40749, WO 96/40772, WO 01/38342, WO 01/091780, WO 2004/101611, WO 2004/100997, WO 2004/101600, WO 2004/101606 and WO 2006/050959) thus appear to be highly suitable for specifically initiating and controlling the re-formation and regeneration of the tissue in question in the case of damage to the skin and mucous membrane, in the case of open skin and flesh wounds and also in the case of skin irritation due to burns or scalds, and ultimately promoting and accelerating healing.

It would thus be desirable to have available EPO, EPO derivatives, EPO peptide mimetics and other protein or peptide active compounds with a similar or different action for these applications in the form of a preparation to be applied topically. Since the half life of EPO in plasma is only about 48 hours, an inadequate or at least unsatisfactory action generally arises in the case of topical use, which cannot be significantly improved even by pegylation or dimerization of the molecule and the consequent extension of the plasma half lifes.

The object is thus to provide, in particular, EPO and its bioequivalent derivatives, fragments, mimetics and the like, but also other proteins or peptides which are suitable or effective for wound healing, for topical use in the said wound indications without dramatic losses of activity occurring due to proteolysis owing to enzymatic or other processes in the wound.

DESCRIPTION OF THE INVENTION

The object set can surprisingly be achieved by a specific, novel plaster comprising the active compound in question, which, due to its novel design and technical provisions, is capable of reducing or even preventing proteolytic cleavage of the active-compound protein, and is able to attain the controllable regionalized therapeutic action of active compounds such as EPO in order thereby to stimulate directly local stem and precursor cells.

The system can furthermore also be used to supply active compounds for the entire organism, where the dosage cannot be achieved as usual hitherto via concentration changes of the active compound.

The aim is to achieve increased safety in spite of improvements in the user friendliness. The difficulties in the usual procedure are that over- and underdoses may occur due to concentration changes which are not evident to the user. Visual checking by the end user is not possible. The risks of systemic administration are hereby reduced and the therapeutic index in relation to systemic side effects is reduced. Before generic uptake, the therapeutic protein, in particular, is degraded by regional proteases. This corresponds to the barrier function of the skin.

In order to support tissue-protective or regenerative use, the use of a sub-polycythemic concentration below 90 U/kg of body weight has therefore been considered (WO 2005/070450). However, this concentration has the disadvantage that only weak regenerative effects occur here, which are substantially limited to endothelial cell formation. High local concentrations which contribute to stimulation of the beta CR sub-unit of the EPO receptor are only achieved to an insufficient extent. The reason is that these are not cells which, like endothelial cell precursor cells, circulate in the blood. Skin precursor cells are present in the dermal components or also crypt structures of the dermis. These can be addressed much more directly by topical application and in particular independently of the systemic administration limits, which are difficult to set and have a lot of side effects. In addition, a higher therapeutic index is thereby achieved since the processing and degradation of EPO can also already be achieved locally in the wound by proteases.

The dual advantage of the ability to set a higher regional active-compound concentration at the site of action and the improved therapeutic index for the entire organism in respect of the concentration, which must be calculated as IU/kg of body weight, is supplemented in combination with the plaster according to the invention by the advantage of wound covering, moisture control and also the possibility of dosage adjustment via the size of the plaster.

Wound plasters which comprise an active compound and are capable of releasing the latter to the wound are known in principle.

Thus, WO 03/101361 describes an active-compound release system in the form of a plaster in which a flowable support comprising a medical active compound which is released to the wound is located in a pocket formed by an upper impermeable layer and a lower permeable layer of the plaster.

WO 2006/109325 describes a plaster, similar in principle, in which a liquid or flowable active compound is located in a small container on the upper side of the plaster. The container can be opened specifically, causing the active compound to come into contact with an underlying layer and to be absorbed thereby. This layer then releases the active compound to the underlying wound.

Neither plaster solves the problem described above for protein-containing active compounds.

The present invention is based on the knowledge that the simultaneous release of active-compound protein from the plaster and removal or separation of proteolysis-promoting wound secretion which forms continuously on/in the wound beneath the wound-covering plaster during the healing process significantly increase the half life of efficacy of the protein on or in the wound, even in extremely small regions of the plaster, and achieve values which correspond at least to the half life of the same protein which could be achieved in the plasma, and frequently even exceed these values.

In order that this takes place, the plaster according to the invention is divided into microdomains of similar or identical geometry, where the microdomains essentially encompass one or generally more sealed cavities which are located in the support matrix of the plaster and represent minidepots or clusters of minidepots for the protein active compound, and encompass one or more open cavities, which are generally channels or channels with local widenings, which are connected to one another and which surround the closed cavities (containers/depots) or clusters thereof. In accordance with the invention, a depot structure is adjacent to a channel structure and vice versa.

The "open" cavities, or channel structures, have the job of removing the wound secretion from the environment of the microdomains or minidepot or clusters of minidepots and preferably transporting it to larger or main cavities in the plaster, from where it can be removed from the plaster. The wound secretion can be actively sucked out (in the simplest case by means of a syringe) by means of corresponding connections, which are preferably attached to the main cavities, or taken up passively by drains, which are preferably introduced into the cavities, in particular main cavities, and develop a capillary action therefrom.

These design measures mean that the active-compound protein released successively to the wound from the depots is, surprisingly, only subjected to the proteolytic activity of the wound secretion enzymes to a slight extent, or not all, meaning that an adequate action in the sense of the above-mentioned regeneration of vascular and especially tissue structures is observed over an extended period.

In the case of EPO, it is thus entirely sufficient to change the plaster every 48-72 hours, depending on the amount of EPO employed, in order to achieve the desired effect, while in the case of topical administration by means of a prior-art plaster or direct introduction into/onto the wound, for example by means of a gel or an ointment, the said non-haematopoietic action does not occur or only does so in an unsatisfactory manner.

Within the said 48-72 hours (the period may be shorter or longer in the case of other protein active compounds), the wound secretion can or should repeatedly be discharged, for example by sucking out by means of the connections provided. If this is not possible or only possible with difficulty, such as, for example, in the case of wounds in the oral cavity or in the jaw region (for example in the case of emergency surgery, jaw operations or tooth transplants, tooth extractions), the same effect can be achieved if the channel-like domains or structures instead contain drainage material which continuously absorbs wound secretion and thus proteolytic enzymes in the microenvironment of each depot or minicontainer which contains the protein active compound and separates it from the protein active compound.

However, the cavities or channels in the microenvironment of each depot in the plaster structure do not, in accordance with the invention, serve just for transport or the absorption of wound secretion, but also for the supply of air and/or other active compounds and/or cells, or cell constituents, which promote healing as a whole. The supply of assistants of this type takes place in accordance with the invention as required and individually via one or preferably more connections or ports provided at certain, preferably regular separations along the channel-like structure, preferably at crossing points or widenings.

Other active compounds of this type can be other growth factors, disinfection agents, antibiotics, proteinase inhibitors, collagen and the like, which can be introduced into the plaster structure through the said connections.

It is also possible in accordance with the invention to introduce cells, preferably autologous cells, such as fibroblasts, endothelial cells, macrophages, monocytes, collagen/elastin fibre cells, or also stem cells, which promote and accelerate tissue and vascular regeneration and thus wound healing, into the wound if required via these connections.

The support structure of the plaster thus encompasses sealed cavities, which serve as containers for the medicament. However, it also encompasses open cavities, usually in the form of channels, which are connected to one another and surround the containers or clusters of containers at a separation which ensures continuous removal of the wound secretion via the channels.

The invention thus relates to a plaster 2 for supplying normal and/or damaged skin, mucous membrane or open wounds with an active compound or medicament 4, comprising a support matrix 6 which comprises the active compound or the medicament 4, where the support matrix 6 encompasses regions (i) in the form of one or more structures serving as container or depot 8 for the medicament, and regions (ii) in the form of one or more cavities 10, which serve for the accommodation and discharge of wound secretion and/or aeration and/or topical introduction of further active compounds and/or cells which promote healing of the skin, mucous membrane or open wounds, where (a) at least one region in accordance with (i) is adjacent to at least one region in accordance with (ii), (b) regions (i) and (ii) are sealed on the side facing away from the wound, so that said medicaments 4, said further active compounds, said cells and wound secretion are delimited and also cannot penetrate through the delimiting layer 12, (c) regions (i) and (ii) are open on the side facing the wound or at least said medicaments, wound secretion and further active compounds/said cells are able to pass through them, (d) regions (ii) formed as cavities 10 are arranged in the plane of the plaster surface in the form of channels, channel-like structures 14 and cavity-like extensions of the channel structures 14, and (e) regions (ii) formed as cavities 10 have at least one connection/opening/port 16 for a syringe or suction/feed device, which enables either wound secretion which has collected in the cavities 10 to be discharged with generation of a reduced pressure in the plaster 2 and/or said further active compounds to be administered if desired.

In accordance with the invention, wounds of the skin or mucous membrane are regarded as being all those that have occurred due to mechanical, thermal or chemical influences, due to radiation or due to illness-induced and/or inflammatory processes (for example eczema, abscesses, allergies, rashes of all types, etc.).

In the case of skin or wounds which are strongly weeping or produce a lot of wound secretion, the cavities in regions (ii) can additionally have drainage means which likewise enable wound secretion or moisture which has collected in the cavities to be discharged. In the case of dryer injuries, for example in the case of sunburn or relatively minor burn injuries, it is also possible to employ a plaster which is not provided with additional drainage means.

In accordance with the invention, the structures in regions (i) serving as container or depot for the medicament are trough-shaped, where the open side of the troughs faces the wound, and the troughs have any desired, irregular, but preferably regular, in particular rectangular, square, hexagonal/honeycomb-shaped or round base area. They preferably have a hexagonal/honeycomb-shaped base area shape.

In accordance with the invention, an individual minidepot or container in regions (i) has an internal depth or thickness in the support structure of the plaster of 0.2 to 5 mm, preferably 0.3 to 3 mm and in particular 0.3 to 2.0 mm. The said thickness or depth of an individual minicontainer of this type depends on the desired depot action of the active compound to be achieved: thicker plasters can accommodate more active compound, and the release to the wound takes place for longer. Deviations in the dimensions downwards into the nano range and also upwards into the macro range are possible at any time in relation to the application and material requirements.

The internal diameter of an individual container or an individual chamber in the support matrix of the plaster can be between 0.2 and 5 mm, preferably between 0.5 and 5 mm, in particular between 1.0 and 3 mm, and thus determines the area with which the active-compound depot has contact with part of the wound. Surprisingly, it has been found that, in particular in the case of an internal diameter of a container of between 1 and 3 mm, the efficacy of the protein active compound released to the wound is greater than in the case of cavities having a significantly larger contact area to the wound.

As already mentioned, the cavities serving as container or depot for the medicament can be assembled to give clusters of 2 to 200 containers, which are separated from one another by thin webs. The cluster structures, like the individual depot structures formed by them, can have different geometrical base area shapes. Thus, the latter can be, for example, rectangular, square, honeycomb-shaped (hexagonal) or round.

The webs between the containers are advantageously of the material of the support matrix and have a thickness of between 0.1 and 3 mm, preferably between 0.1 and 0.5 mm. The webs between the honeycomb-shaped containers or minidepots can in accordance with the invention themselves have channel-like structures (for example in the form of a hollow profile), which serve for the discharge of wound secretion and/or aeration and/or the supply of further active compounds/said cells. Webs which have a hollow profile have a thickness of preferably between 0.5 and 3 mm and are installed, in particular, where individual depots have been assembled to give relatively large clusters, and the area with which a cluster covers the wound is sufficiently large that the channel structure surrounding the cluster domains is not sufficient to be able to transport away the wound secretion collecting under the cluster domains, which are large in this case.

For this reason, a cluster should have an average diameter which should not be significantly larger than 25 mm and is preferably between 5 and 25 mm, depending on how large the individual containers of the cluster were selected. A corresponding cluster structure can have between 10 and 200, preferably between 25 and 100, minidepots or individual structures in regions (i).

It has been found to be advantageous for the entire area occupied by the channel-like cavities in regions (ii) of the plaster to be >1%, >5%, >10%, >20%, >30% or >40% of the area occupied by the depot domains in regions (i). The area of the channel structures preferably corresponds to 2-30%, preferably 5-20%, of the area of the depot structures. Ultimately, the ratio depends on the type and amount of the tissue and wound liquids being secreted. In the case of heavily weeping or secreting wounds, the channel-like structures in regions (ii) should occupy about 20 to 40% of the effective total area of the plaster, while in the case of wounds producing only little wound secretion, a corresponding proportion of 2-10% is sufficient.

The invention thus relates to a corresponding plaster in which the thickness of the medicament-containing structures (i) is 0.2 to 5.0 mm, preferably 0.3 to 2.0 mm.

The invention furthermore relates to a corresponding plaster in which an individual structure in regions (i) has an average diameter or separation of its opposite edges of 0.5 to 5.0 mm.

The invention furthermore relates to a corresponding plaster in which the individual structures in regions (i) are assembled in clusters which have an average diameter or separation of their opposite edges of 5.0 to 25.0 mm, preferably 10.0 to 15.0 mm.

The invention also relates to a corresponding plaster in which the individual medicament-containing structures in regions (i) are assembled in clusters, where each cluster preferably has up to 200, in particular 25 to 100, trough-like individual structures in regions (i).

The channels or channel-like structures in regions (ii), which generally have a hollow profile with an open side to the wound, have an average internal diameter of 0.3 to 3.0 mm. A plaster according to the invention can have channels of different thickness or diameter in the form of main and secondary channels. In particular, the main channels can have a larger diameter at regular or irregular separations over a small region, resulting in the presence in this region of a small cavity in the form of a bubble, sphere or dome having a diameter which is greater than the channel itself.

Widenings or thickenings of this type are preferably provided in the crossing area of two intersecting or meeting channels, but can also be provided independently thereof along a channel. In the crossing area of two intersecting channels, these widenings cause more rapid and continuous supply or discharge of wound secretion or the above-mentioned other active compounds, cells and other assistants. It is therefore advantageous to provide at least some of these widening areas with connections/openings/ports for removal by suction, preferably by means of correspondingly designed syringes, or for the supply of the said substances, or for aeration of the wound.

In the plaster according to the invention, regions or domains of structure (i) (active-compound depots or clusters of active-compound depots) alternate with regions or domains of structure (ii) (channels), where, as already mentioned, excessively large regions without channels must be avoided in order not to reduce the active-compound effect due to excessive wound secretion present. Thus, the separation between two channel-like structures in regions (ii), and thus also the separation of two depot structures (i) or cluster structures, should be between 5 and a maximum of 25 mm, preferably between 6 and 15 mm.

The invention thus also relates to a corresponding plaster in which the channel-like structures (ii) have an average diameter of 0.3 to 3.0 mm, where main channels have a thickness of between 1.0 and 3.0 mm and secondary channels have a thickness of between 0.3 and 1.0 mm.

The invention also relates to a corresponding plaster in which the separation between two channel-like cavities in regions or domains (ii) is a maximum of 25 mm, preferably 5 to 25 mm.

The invention furthermore relates to a plaster which has intersecting channel-like cavities in regions/domains (ii), and the connection for a suction/feed device is installed in the crossing area of two channel structures of this type in regions (ii). At least some of these crossing areas are preferably widened in a cavity-like manner in order to provide more space for collected wound secretion and the suction device, which, in the simplest case, is a connection port or an opening for a syringe or suction pump.

In this sense, the invention therefore also relates to a plaster which has intersecting channel-like structures in regions (ii), and one or more of the crossing areas formed are enlarged in a dome-, bubble- or sphere-shaped manner.

The invention furthermore relates to a plaster which comprises cavities or channel-like structures in regions (ii) which do not intersect or cross, but instead are arranged in a ring- or spiral- or meander-shaped manner and alternate with or are adjacent to rings, spirals or meanders, where two domains of the same type have an average separation from one another of a maximum of 25 mm, preferably 5 to 25 mm.

The arrangements of cavities (i) and (ii) on the plaster according to the invention can differ in their geometry and relation to one another. In the simplest case, a plaster consists of vertical and horizontal, preferably in each case parallel channel structures in regions (ii) which intersect at the crossing points and surround corresponding geometrically shaped regions or domains in regions (i) which contain the active-compound depots or containers. An in principle rectangular, square or diamond-shaped three-dimensional grid of channel structures and depot structures is thus formed in the support matrix. A channel or the edge thereof and the adjacent depot structures do not necessarily have to be straight, but instead may also be waved, zigzag-shaped or irregularly aligned.

In a further embodiment of the plaster according to the invention, the two cavities in regions or domains (i) and (ii) can mutually surround one another in a ring-, oval-, ellipse- or rectangle-shaped manner, i.e. a correspondingly shaped channel cavity is adjacent to a correspondingly shaped domain comprising depot cavities, where the separation between two cavity domains of the same type is a maximum of 25 mm, preferably 5 to 25 mm. In the simplest case, the individual channel-like cavities are not connected to one another. By creation, for example, of a vertical and/or horizontal main channel, which cuts through the respective ring-like domains, all channel-like cavities of the plaster are then connected to one another.

Alternatively, in a further embodiment of the plaster according to the invention, the two structures in regions (i) and (ii) can surround one another in a spiral- or meander-like manner, where the separation of regions of the same type is again between about 5 and 25 mm. In this embodiment, only one channel structure in region (ii) and only one depot structure in region (i) are in principle present in the support matrix, where, in a further variant, crossing channel structures in regions (ii) can also be included here.

Also in the embodiments in which the channel-like cavities in regions (ii) do not cross, these structures preferably have bubble-, dome- or sphere-shaped widenings or cavities to which connections are attached or in which drainage material can be accommodated.

The plaster can be structured or built up in such a way that an individual active-compound container is completely surrounded by channel-like structures. Such plaster arrangements have a high proportion (20-40%), based on the total area, of channel structures and are particularly suitable if a large amount of wound secretion has to be removed uniformly (FIG. 1c). In many cases, it is sufficient to assemble the depot structures in the form of clusters, where channel-like structures in regions (ii) are merely present between the cluster structures. In this case, the area proportion of the channel structures in the plaster arrangement is relatively small (2-10%) (FIGS. 1a, b, d). In this arrangement, a particularly large amount of active compound can be provided per unit area. By increasing/reducing the channel diameters or the thickness/-depth of the depots or plaster, the individual parameters mentioned can be adjusted individually within a certain range.

The plaster according to the invention can be provided with a self-adhesive tape, known per se, which is attached to the edges of the plaster, enabling the wound to be sealed off in an air-tight manner. Furthermore, this also seals the support matrix of the plaster, including its channel-like structures (ii), in a pressure-tight manner, so that, if a connection for, for example, a syringe or a suction device is present, wound secretion can be sucked out with generation of a reduced pressure. The generation of a reduced pressure additionally has the effect that active compound can be released from the depot to an increased extent and can be introduced into the wound, which is now free from wound secretion, in order thus to achieve the optimum pharmacological effect therein.

The invention thus relates to a corresponding plaster which is additionally provided with a self-adhesive attachment means which completely seals off the support matrix with the medicament/active compound and thus the wound in an air- and pressure-tight manner.

The plaster can also be provided without adhesive tape or adhesive closure and attached to the wound by other means, for example a bandage. In this case, the plaster, owing to its plot-like microdomain structures can be cut not only to size, but also in relation to the amount of active compound to be administered. Dosage merely via the plaster size is thus also possible, which was hitherto not known in any other prior-art plaster.

If the plaster is used without integrated adhesive tape, pressure tightness can be achieved, for example, by means of a separate adhesive tape which is stuck or attached over the plaster or parts thereof.

If the plaster according to the invention has to be employed entirely without the use of an adhesive tape, as is unavoidable, for example, on use on the mucous membrane, for example in the oral cavity, it should at least be provided with drainage material instead of a connection for a suction device in order that wound secretion can be removed by the suction action of the drain. Thus, the plaster according to the invention can also be placed in wounds in the form of tailored strips and pads in the case of dental treatments, tooth extractions, treatments of the tooth socket and jaw operations. The drain suitable for these, but also other cases can consist, for example, of a collagen fleece or a gelatine sponge or other materials used for this purpose in the prior art. A material of this type can also be used in order to cover the wound with the plaster element, it also being possible to employ fibrin adhesive preparations. If desired, the mucous membrane wound can be sutured in order to reduce the fibrinolytic influence of saliva.

In the case of particularly dry changes to the skin, as can occur, for example, in dermatological diseases with and without erythema, in the case of skin reddening, such as, for example, sunburn, or also normal skin states, the plasters can also be used without drainage channels or without opening thereof.

The active compound or active compounds can be introduced into the depot structures in regions or domains (i) in a wide variety of ways. Thus, for example, the active-compound protein can be pressed into the individual cavities in solid form, for example in lyophilized form or, if desired, also as a solid protein powder. The specific geometry (for example honeycomb-shaped base area) and size of the depot cavities in the support matrix, which results in a relatively large surface area compared with the volume, means that additional support substances are not necessary in the simplest case.

However, the depot chambers may also contain the active compound in dissolved form or as a suspension. In this case, the depot domains must be provided with a protective film, which is removed before application of the plaster to the wound. Besides a protective film of this type, which is impermeable to any active compounds and liquids in the depot chambers, and can also preferably be employed if the active compound is compressed in solid form or has been taken up in a non-liquid support material, a permeable or semipermeable film which allows molecules of the protein active compound and/or, where appropriate, the other active compounds to pass through in a delayed manner and migrate into the wound, but, by contrast, does not allow proteolytic enzymes or bacteria out of the wound in the reverse direction, and directly covers the depot chambers may also be provided in accordance with the invention. Corresponding films of this type can also be made from biodegradable materials, as mentioned below in greater detail. Films or membranes of this type are adequately known in the prior art.

The invention thus relates to a corresponding plaster which has, on the side facing the wound or skin, a protective film, which is removed before use.

The invention also relates to a corresponding plaster which has, on the side facing the wound/skin, a film or membrane which is permeable to the medicament and, where appropriate, impermeable to proteolytic enzymes or other undesired substances having relatively large molecular weights from the wound secretion.

The invention also relates to a corresponding plaster which comprises a film or membrane made from a biodegradable material.

However, the protein active compound may also be present in an active-compound reservoir in the form of a porous matrix. A porous matrix of this type can be a synthetic or natural porous support, for example polymeric substances, such as hydroxymethylene acrylates, polyethylene glycols, polyethylene oxides. These materials can be crosslinked by irradiation or other known methods in order to ensure insolubility in water.

Also particularly suitable are biocompatible or bioabsorbable support substances, such as polysugars, polyvinyl alcohols, polylactides, polylactic acid, polyvinylpyrrolidone, poly-L-lysine or also lactic acid-glycolic acid copolymer. The medicament substances can, however, also be bound in a collagen sponge which is accommodated in the depot chambers.

However, the protein active compounds and other active compounds may also be embedded, dispersed or dissolved in so-called microspheres or surrounded thereby. Microparticles in accordance with the invention include liposomes and nanoparticles having a size between 10 nm and 2 mm. Suitable materials for the production of microspheres are, for example, crosslinked dextrans, ceramic materials or of course also synthetic polymers, such as polyurethanes, polymethyl methacrylates, polyethylene terephthalates, polystyrenes, polyolefins, polyacrylamides, polylactides, polyglycolides and other synthetic polymer materials which are suitable for biomedical applications. The corresponding microspheres, which are charged with the active compound, are introduced into the depot chambers, where they release the active compound(s) to the wound in a controlled and delayed manner.

Besides the protein active compound, other active compounds and also cells which promote wound healing may, as already mentioned a number of times, also additionally be present in the depot cavities in regions (i). For example, proteinase inhibitors, such as, for example, aprotinin, or also antibiotics, which are helpful in the case of infected wounds, may be useful. Xenogenic or autogenic, but in particular autologous cell preparations, which include, for example, fibroblasts, endothelial cells, macrophages, monocytes or also stem cells, individually and in mixtures, which support wound healing initiated by the primary active protein, may likewise be present.

Suitable as support matrix for the plaster according to the invention are in principle all known plaster materials which facilitate the production of a microdomain structure, as described. Particularly suitable are silicone materials or synthetic rubber, natural rubber or synthetic polymer material made from the substances described in the prior art for this and similar purposes, as described above in principle for comparable materials. The materials used should in each case have the ability correspondingly to facilitate shaping by casting or pressing the material in order to obtain the microdomain structure mentioned. In addition, they should be relatively soft and flexible.

The invention thus relates to a corresponding plaster which comprises a support matrix for the cavities in regions (i) and (ii), and this support matrix is preferably made from a polymeric plastic, silicone or a natural elastomer material which is suitable for the production of the requisite microdomain structures on or in the support matrix, for example by cutting, casting, pressing and similar processes.

In general, the plaster according to the invention is suitable for use for a very wide variety of pharmacological active compounds, but is preferably suitable for proteins or polypeptides, as discussed in detail in the introduction. The particularly advantageous properties can, in particular, be achieved for proteins and polypeptides having a molecular weight or less than 50 kD, preferably between 10 and 50 kD, where proteins, which are in principle easily attacked by cleaving enzymes or infecting cells, give very good results in relation to efficacy and extended half lifes. Proteins of this type are, for example, cytokines and growth factors, such as EGF, TGF beta, GSF, GM-CSF, HGH, CNTF, EPO, TPO, interferons, such as IFN alpha, IFN beta, IFN gamma, and interleukins, such as, for example, IL-2, IL-7, IL-6, IL-8, but also blood-clotting factors, such as, for example, thrombin, haematin and the like.

As already described, the plaster according to the invention exhibits particularly good results with the active compound erythropoietin (EPO) derivatives and fragments thereof and peptide mimetics and peptide analogues having the biological haematopoietic and in particular non-haematopoietic biological activity of EPO. A plaster according to the invention which is charged with EPO enables wound healing of a skin, mucous membrane or flesh wound to be crucially favoured.

It has been found here that EPO in a weekly dose of greater than 100, preferably 100-500 IU/kg of body weight (1 µg of recombinant human EPO corresponds to 130 IU) can ensure accelerated wound healing in injuries, in particular also in the jaw and dental region, if it is applied topically via a plaster according to the invention. Since a plaster of this type should preferably be changed between 48 and 72 hours, it is necessary, but sufficient for a plaster of this type to comprise about 25-175 IU/kg of EPO in order that a satisfactory effect can be achieved. However, doses per plaster of greater than 200 IU/kg of body weight or more may also be provided if the plaster is changed two to three times per week. In highly dosed forms of a plaster (greater than 300 IU/kg), a plaster of this type can also be retained for seven days. It should be noted that the amount of active compound and the kinetics of its release can ultimately also be controlled in accordance with the invention through the thickness of the depots.

For other protein active compounds, similar doses can be used, or they follow the doses which are also usual in the case of systemic administration.

The invention thus furthermore relates to a corresponding plaster in which the medicament introduced into the cavities in regions (i) is a polypeptide or protein which preferably has a molecular weight of 10-50 kD and is optionally proteolysis-sensitive or can easily be cleaved by enzymes and bacteria present in wounds.

The invention relates, in particular, to a corresponding plaster which comprises a growth factor or a cytokine, preferably EPO or a peptidic molecule having the biological activity of EPO.

Finally, the invention relates to the use of a plaster as described above and in the claims for covering wounds and to the use of EPO and other suitable growth factors and cytokines for the production of a plaster, as described above and in the Claims, for the regenerative healing of damaged skin, mucous membrane or open wounds.

FIG. 1a shows the structure of an embodiment of the plaster according to the invention in three-dimensional view. The depots for the active compound have a honeycomb-shaped structure and are assembled to give clusters of about 50 individual depots, which are separated from one another by grid-like channels.

FIG. 1b shows a similar embodiment to FIG. 1. The channels are formed in polygonal lines corresponding to the honeycomb structure of the depots. Openings for the connection of a syringe or suction device or feed device are provided at the crossing points of the channels.

USE EXAMPLES OF THE PLASTER ACCORDING TO THE INVENTION

Figure 1A:
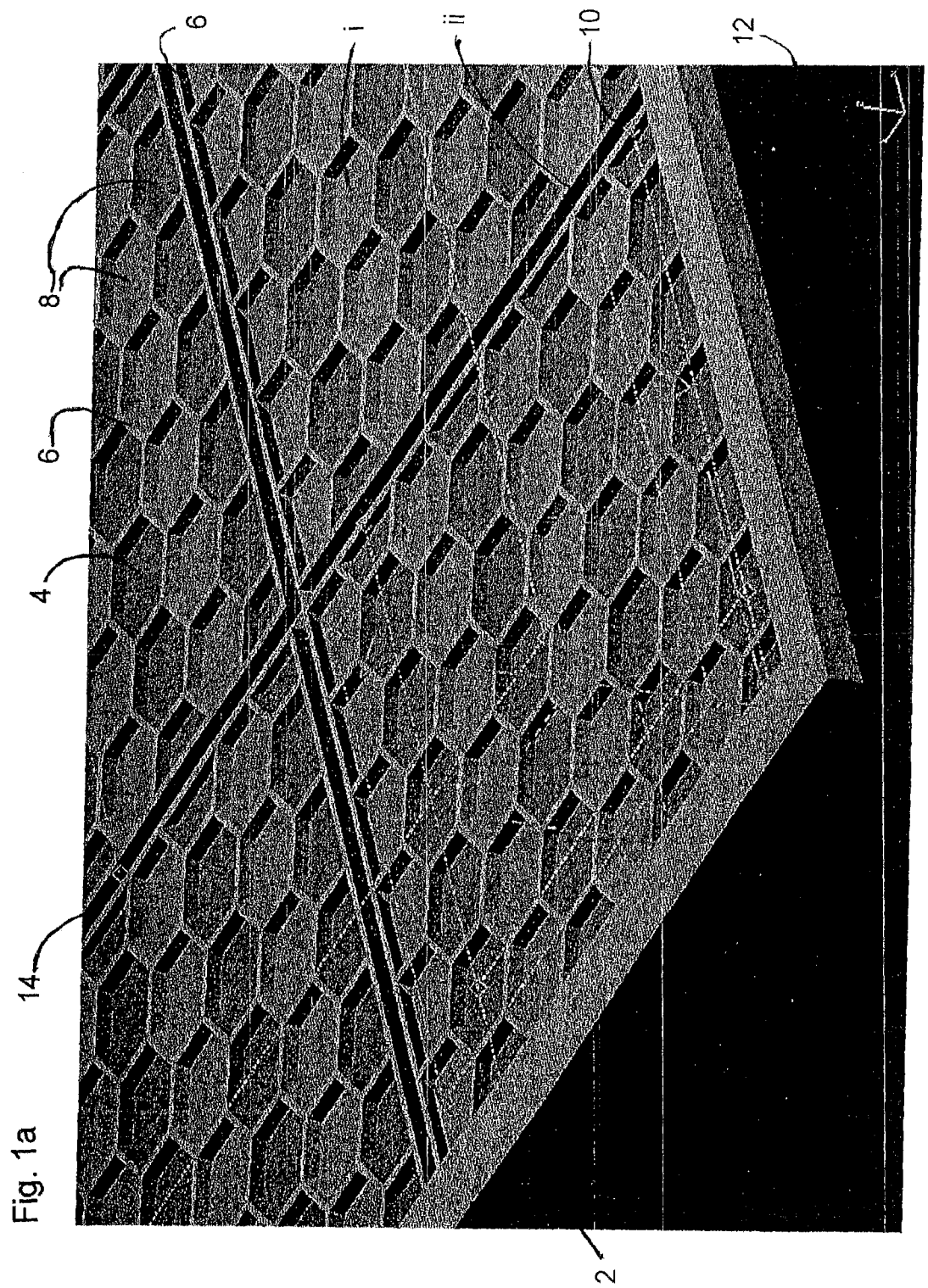
FIG. 1c shows the section of a plaster according to the invention with honeycombs as depot for the active compound, but each individual depot is completely surrounded by channel cavities. A widened crossing zone with an opening for discharge or feed is shown at the bottom right edge.
FIG. 1d shows a plaster according to the invention analogously to FIG. 1a in original size.
Figure 1B:
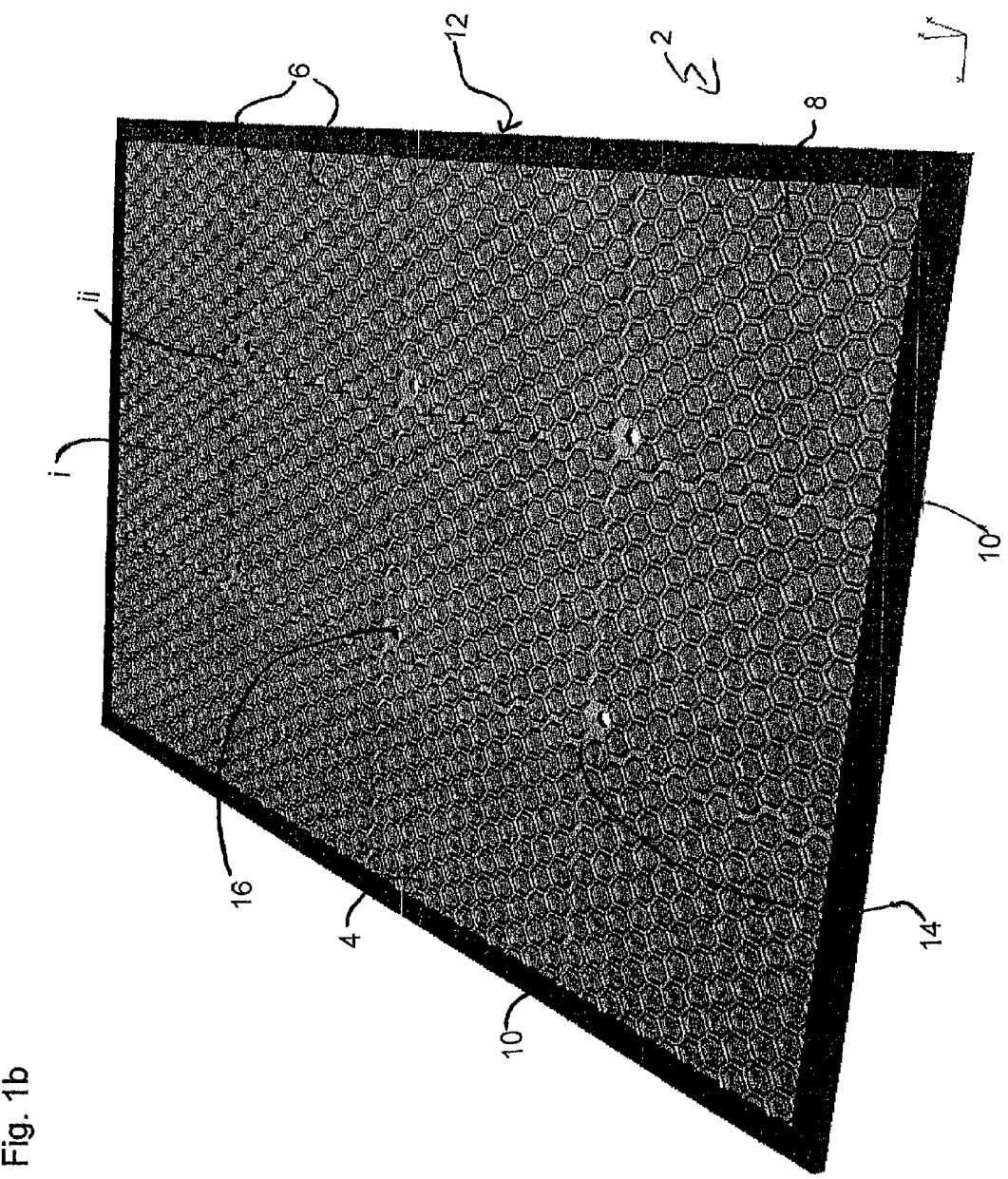
Figure 1C:
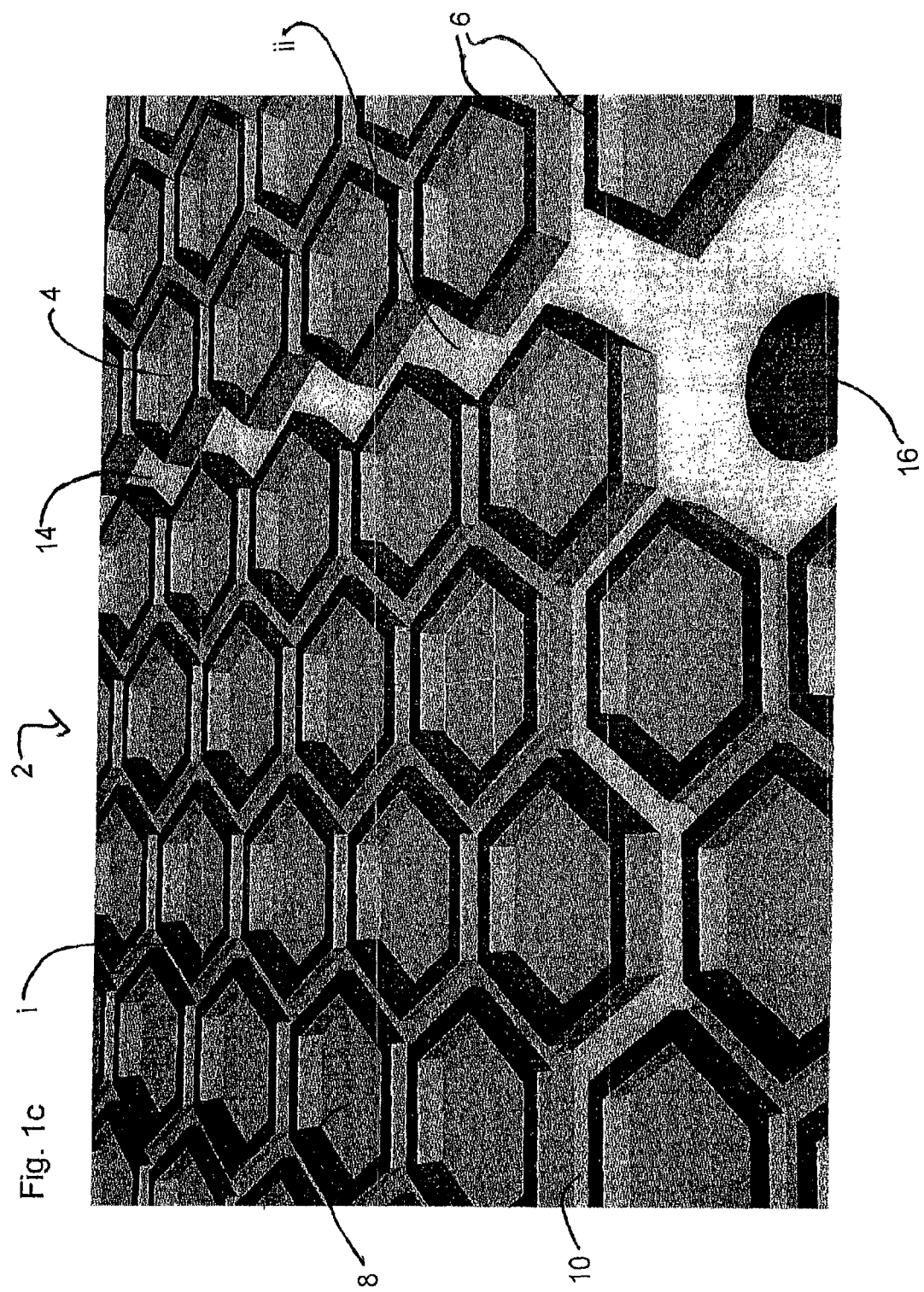
Figure 1D:
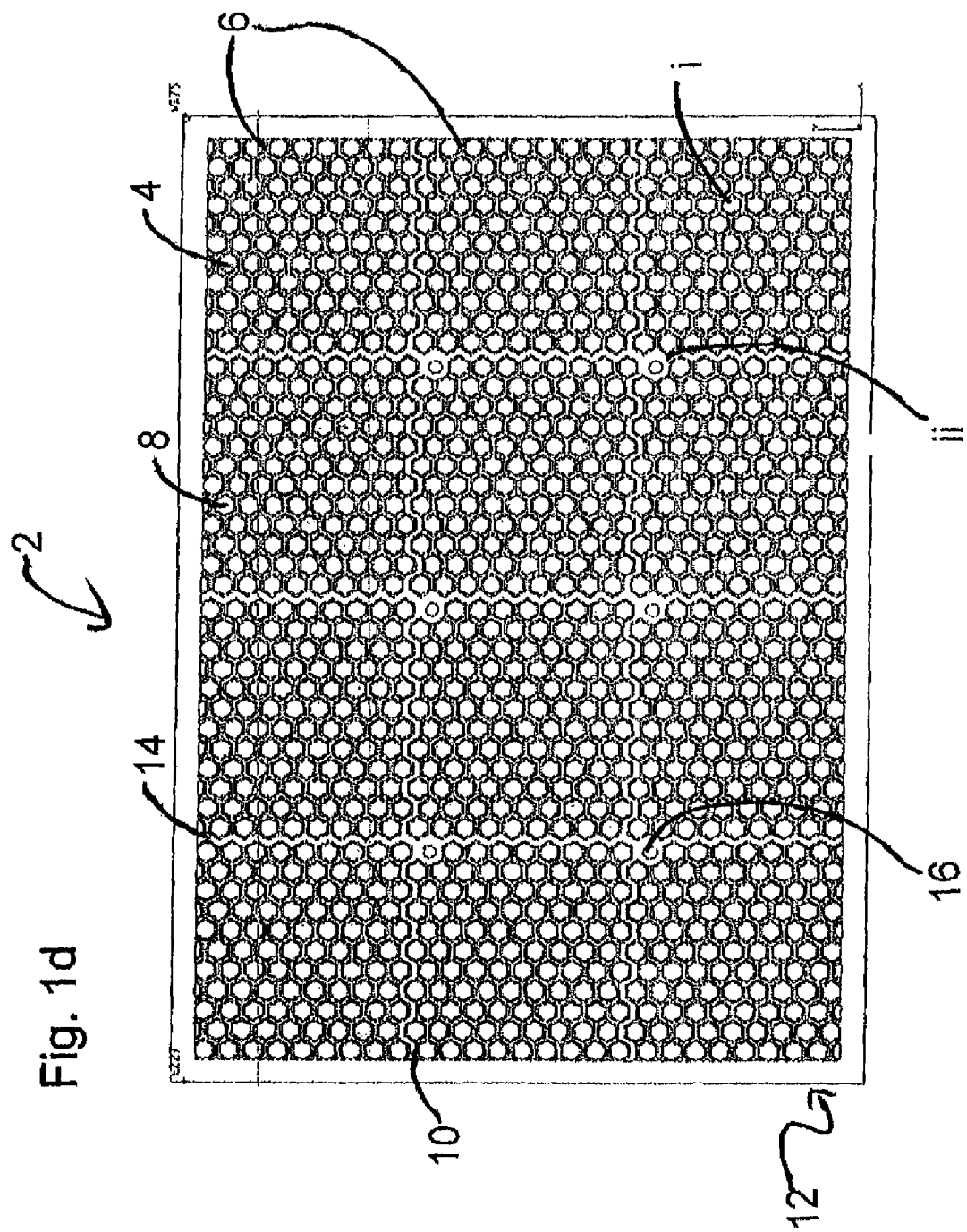

For a deep graze having a size of about four×five centimetres, a plaster is cut out of a larger master plaster measuring about 8×12 centimetres. The plaster has a domain structure as shown in FIG. 1d with the following dimensions: honeycomb-shaped individual depots having a depth of 1 mm and an internal diameter of 2.5 mm. In each case, 80 such individual depots are assembled to give clusters, which are in turn separated from one another by channels having a depth of 1 mm and a width of 1.5 mm. The channels have a grid structure and have at some crossing points a sealable opening, to which a suction device can be connected. The individual depots contain a total of 13,000 IU of EPO (corresponding to about 100 μg). The EPO was introduced in advance in soluble liquid form into the plaster's support structure made from soft silicone, or was uniformly distributed over the cluster structures. The lyophilization of the active compound was carried out on the plaster or in the depot containers. The plaster produced in this way was provided on the open side with a protective film, which was removed before application to the wound. The plaster was applied to the fresh, but no longer bleeding wound and attached to the healthy skin and sealed in an air-tight manner using an adhesive tape. Wound secretion was sucked out initially every three hours, later every six hours, by means of a small syringe which was attached to one of the connections on the plaster. After 48 hours, the plaster was changed. The wound secretion was then sucked out only 1-2 times over the course of 24 hours. The plaster was changed again after a further three days, during which sucking-out was only carried out once. The healing state was checked and characterized on each change of the plaster.

By comparison, a gel formulation comprising EPO in the same dose as indicated above was applied to a comparable wound. After the same times as in the case of the plaster, the gel application was renewed and the progress of healing was noted. The wound with the plaster healed more quickly in each phase and was finally healed after only 60-80% of the time compared with the corresponding gel formulation.

In the case of sunburn with intense reddening of the skin and incipient peeling, the plaster with a hydrogel comprising EPO in a concentration of 100 IU/kg and week present in the cavities is placed over a large area covering the damaged areas. The softness of the silicone material used gives a snugly-fitting and immediately pain-killing effect since loss of moisture from the skin is prevented and a pleasant local cooling effect on the skin is achieved by the retention thereof in combination with, for example, a methylcellulose gel used. In order to stimulate the still-vital stem cells of the skin in the hair follicles in the dermal region, EPO can now act directly on these cells and accelerate regeneration of the skin without having to follow the indirect route via systemic administration. This prevents polycythemic effects. EPO is broken down in the skin at the same time. The healing of the sunburn is accelerated, so that an optimum course is already evident after 2-3 days, whereas the same effect is only observed after 4-5 days on use of the same hydrogel with the same concentration of EPO without a plaster.

In the case of poorly healing wounds, such as, for example, ulcers in diabetes, the plaster can be applied directly to the wound area, after cleaning of the wound, so-called debridement, with overlapping to still-intact areas. However, these poorly healing wounds still have stem cells, such as CD90+ cells, which are present in the wound areas together with CD31+ cells. Direct stimulation of these cells enables rapid establishment of the therapeutic active-compound concentration without having to follow the indirect route of systemic administration. This has the advantage that, precisely in these chronic wounds, accumulation phenomena and risks of systemic administration are avoided. The so-called sub-polycythemic doses of less than 90 U/kg of body weight are of less importance here since on the one hand not only the endothelial precursor cells are intended to be stimulated, but, in particular, the local tissue-specific precursor cells for the skin with the dermis, skin appendage and epidermis components are intended to be stimulated to scar-free healing. The dose can thus be calculated as units/per area. It has been found that, in particular, tissue-specific stem cells require a dose considerably greater than the so-called sub-polycythemic dose in order to be stimulated in an optimum and clinically relevant manner. The proportion of vessels in the volume of the skin is only a few per cent. However, more than 90-95% are specific tissue structures. Due to the interaction of a strong regional concentration, all local stem cells can not only be addressed rapidly and clearly, but also react. Systemic administration would have to address all cells on the route to the site of action and would therefore address not only endothelial cells, but also any cells containing this receptor. It has been found that the cells in the skin carry the receptor (betaCR) which is responsible for tissue protection, and these are not endothelial cells. The advantage of topical application with the plaster additionally consists in that, besides the possibility of controlled removal of wound secretion, the active compound can be introduced directly into the wound area uninfluenced thereby. To this end, the active compound can be introduced, for example, via gel or ointments, micelles and lipogel applications. In a simplified variant, the cavities can, however, also contain the active compounds in dry, for example lyophilized form. This then facilitates particularly intimate contact with plasma and blood constituents on the freshly cleaned wound. The polymerization thereby initiated creates a micromedium which is particularly conducive to wound healing and is free from interfering factors and thus provides optimized conditions for regional stem-cell differentiation, which ultimately facilitates structural regenerate of high quality without scarring. Since vascular stimulation has only an initiating involvement in these events, topical application with improved integration of tissue-specific stem cells can result in a virtually normal regenerate. Chronic wounds, which previously often did not heal over years, now heal in 1-2 weeks of plaster application. In addition, the wound can thereby also be kept dry and sterile using a single system. The wound secretion that still occurs in the initial phase can be kept clean by the patient by connection of a 50 ml syringe to one of the ports or connections. In addition, aprotinin and/or antibiotics from the depots can act as mentioned above.

The doctor or patient can also rinse the wounds in simple form without having to run the risk of removing all active compound at the same time.

2nd-degree Burn Wounds or Donor Sites of the Skin After the Taking of Split-skin Grafts:

In the case of deep 2nd-degree wounds, there are still stem cells in the skin which can be attributed to direct application of EPO for scar-free or low-scar healing of the skin. After split-skin grafts have been taken or after so-called dermal abrasion in cosmetic interventions for scar correction on the face, the flexible plaster can be applied directly to the wound, which is initially still slightly weeping. The silicone material of the plaster enables moisture regulation at the same time as a gentle means for sucking out wound secretions. In parallel, lyophilized EPO can combine directly with local plasma and thus create an optimum wound medium which activates the stem cells. Protracted release enables delayed bandage changing in the case of these wounds. A split-skin graft removal can thus heal in 3-4 days instead of after 9-10 days. On use of transparent materials for the plaster, for example silicone, PDMS, or also soft Teflon compounds, the course of healing can even be observed directly without interfering with the sterile environment beneath the plaster. The doctor can thus match his diagnosis rapidly and non-invasively to regional conditions and treat patients gently and with conservation of resources.

Stem-cell Therapy, in Particular in the Case of Deep Third-degree Burns:

In an advantageous use form, the plaster can also be utilized to introduce stem cells into the affected region directly and for therapeutic reasons from bone marrow, fatty tissue, blood or other skin regions. This is particularly indicated if the severity of the damage means that no or virtually no local stem cells are present. This is the case, for example, in third-degree burns since the dermal components have been completely destroyed there. In spite of the presence of vascular precursor cells from the underlying muscle components, the skin is nevertheless unable to regenerate. This also shows the importance of the ability of skin precursor cells to be stimulated topically by EPO in addition to the general and not always desirable systemic stimulations of endothelial precursor cells on systemic administration of EPO with or without sub-polycythemic doses. This effect alone is in no way sufficient to heal a wound of this type.

In an advantageous application of the invention, stem cells can be supplied exogenously via the ports. The plaster here is used like a stuck-on bioreactor. The EPO from the microdomains is released slowly and attaches itself to the stem cells introduced from the bone marrow. These are obtained via needle aspiration (10-50 ml) and reduced to a volume of 1-2 ml by centrifugation. This is slowly added dropwise via the ports and distributed over the wound area. This introduces a high concentration of stem cells decentrally, even over relatively large wound areas. Within 1-2 hours, these cells adhere and can then be fed in a targeted manner into the regeneration process by the EPO exposure. The regional damage environment additionally promotes this growth. The cells can be oxygenated in the initial phase via the oxygen availability of a silicone plaster, which is then advantageously particularly thin, with a material thickness of about 50-100μ. In spite of sterile wound closure, this causes polarized availability of atmospheric oxygen as in normal skin and thus favourable differentiation conditions of the precursor cells in the epidermis and dermis. Extremely severe damage which can otherwise only be treated by split-skin grafts or foreign-skin grafts now heals in 1-2 weeks. As an alternative to cells from the bone marrow, stem cells from hair roots with and without prior in-vitro expansion can also be injected into the ports. Stem cells from the fatty tissue and fat cells from other regions of the body can likewise be injected in combination in order to reconstruct the subdermal fatty tissue. The microstructuring of the plaster is of secondary importance here if the active compound is injected with the stem cells or separately or is a constituent of a support material for the stem cells (for example hyaluronic acid, hydrogels, fibrin, plasma).

Pain Therapy

In chronic patients, who frequently, even at home, have to consider a variable dose corresponding to the pain requirements and owing to side effects, the controllability of doses plays a major role. Conventional plasters comprise a defined active-compound concentration and cannot be divided without damaging depots and without thus endangering the overall action and control. In the case of tablets, however, divisions are usual. Children are given, for example, half a tablet, etc. The advantage of the plaster principle indicated is that concentrations can be adjusted with high precision and with large safety margins not only via the area of the wound, but also via the area of the plaster. A plaster having an area of, for example, $0.5\ m^2$ can easily be divided into four equal parts by the patient. To this end, the channels can in advantageous form be constructed like nominal breaking points, which facilitate simple manual division like in a tablet.

Active compounds where dosing is difficult and variable, such as, for example, antibiotics, sleeping agents, nicotine, morphine, ASS and the entire group of analgesics, can thus be dosed in a manner which is easily controlled by the patient. In order to improve the skin friendliness and absorption, these substances can be introduced into the depots in micelles. The support materials may liquefy or soften due to warming on physical contact and thus release both regionally acting substances, such as, for example, antibiotics in the case of skin infections and also substances having systemic actions in a controlled manner as required and in a dose suitable for the area. In contrast to the wound situation, protease degradation does not play a significant role here, meaning that systemic effects are not prevented.

The invention claimed is:

1. A plaster for supplying at least one active compound or medicament to at least one of damaged skin, mucous membrane and an open wound, the plaster substantially comprising a support matrix which comprises at least one of the active compound and the medicament, wherein the support matrix comprises:

(I) container regions or structures in the form of one or more container cavities serving as containers for the at least one of the active compound and the medicament, and (II) channel shaped regions or structures in the form of one or more flow cavities serving as channel shaped structures, which serve for at least one of collection and discharge of wound secretion, aeration, topical introduction of at least one further active compound and introduction of cells which promote healing of the skin, mucous membrane or open wound, where (a) at least one container region is adjacent to at least one channel shaped region (b) the container and the channel shaped regions are sealed on a side facing away from the skin, the mucous membrane and the open wound, (c) the container and the channel shaped regions are open on the side facing the skin, the mucous membrane and the open wound such that at least one of wound secretions, aeration, topical introduction of a further active compound and introduction of cells is able to pass therethrough, (d) the container and the channel shaped regions, formed as cavities, are arranged in the plane of the plaster surface, and (e) the cavities in the channel shaped regions directly communicate with at least one opening for connection to one of a syringe a suction/feed device, which facilitates at least one of discharge of wound secretions which collect within the cavities to flow along the cavities and be discharged out through the at least one opening due to generation of a reduced pressure produced in the plaster and introduction of at least one of the aeration, the topical introduction of the further active compound and the introduction of cells.

2. The plaster according to claim 1, wherein in a case of weeping or wound-secretion-producing skin or wounds, the cavities in channel shaped regions additionally have drainage means which enable wound secretion, collect with the cavities to be discharged.

3. The plaster according to claim 1, wherein the cavities in channel shaped regions are channels which are connected to one another.

4. The plaster according to claim 1, wherein the cavities in container regions, which serve as containers for at least one of the active compound and the medicament, are trough-shaped, an open side of the troughs faces the wound, and the troughs have one of a rectangular, square, hexagonal/honeycomb-shaped or round base area.

5. The plaster according to claim 1, wherein the cavities in the container regions, which serve as containers for at least one of the active compound and the medicament are separated from one another by separating walls formed of webs of material of the support matrix, and a first container structure shares, at least in part, a plurality of separating walls with a plurality of additional container structures.

6. The plaster according to claim 1, wherein the webs have channel shaped structures which are at least partially connected to one another and serve for at least one of the collection and discharge of wound secretions, aeration, topical introduction of at least one further active compound and introduction of cells.

7. The plaster according to claim 1, wherein the cavities in the container regions, which serve as containers for at least one of the active compound and the medicament, represent sub-structures which are assembled in clusters and are separated from one another by webs of the material of the support matrix.

8. The plaster according to claim 7, wherein the clusters have one of a rectangular, square, hexagonal/honeycomb-shaped or round base area shape.

9. The plaster according to claim 8, wherein the clusters have a square or rectangular base area shape.

10. The plaster according to claim 8, wherein the shape of the base area of the cluster is one of identical to or different from the base area shape of the sub-structures in the container regions.

11. The plaster according to claim 7, wherein a cluster domain in the container region is adjacent to at least one cavity in the channel shaped region.

12. The plaster according to claim 11, wherein the structures in the container regions and the channel shaped regions are arranged so as to form one of a rectangular, a round spiral, a rectangular and a round ring.

13. The plaster according to claim 12, wherein the support matrix has one or more spiral- or ring-shaped arrangement so that its area is essentially filled by this arrangement(s).

14. The plaster according to claim 7, wherein two cluster domains in the container regions are separated from one another by at least one cavity in the channel shaped region.

15. The plaster according to claim 1, wherein a cavity in the channel shaped regions intersects with at least one other cavity in the channel-like regions.

16. The plaster according to claim 15, wherein the cavities in the channel-like regions form a rectangular, square or diamond-shaped network or grid in the support matrix, which surrounds the structures in the container regions.

17. The plaster according to claim 16, wherein the structures in the container regions are cluster domains.

18. The plaster according to claim 1, wherein the cavities in the container regions which contain at least one of the active compound and the medicament have a thickness which is matched to a medicament action to be achieved.

19. The plaster according to claim 18, wherein at least one of the thickness and a depth of the medicament-containing cavities in the container regions is between 0.3 to 3.0 mm.

20. The plaster according to claim 1, wherein an individual cavity in the container regions has an average internal diameter of between 0.5 to 5.0 mm.

21. The plaster according to claim 1, wherein the individual cavities in the container regions are assembled in clusters which have an average internal diameter of between 5.0 to 25.0 mm.

22. The plaster according to claim 1, wherein the individual medicament-containing cavities in the container regions are assembled in clusters, and each cluster has between 20 to 200 trough-like individual structures in the container regions.

23. The plaster according to claim 1, wherein the channel shaped cavities in the channel shaped regions have an average internal diameter of between 0.3 to 3.0 mm.

24. The plaster according to claim 1, wherein a separation between two channel shaped cavities in the channel shaped regions and a separation between two clusters in the container regions is in each case between 5 to 25 mm.

25. The plaster according to claim 1, wherein in a case of intersecting channel-like cavities in the channel shaped regions, a connection for a syringe or suction/feed device is installed in a crossing area of two channel structures.

26. The plaster according to claim 1, wherein in a case of intersecting channel shaped structures in the channel shaped regions, the crossing area is enlarged in the form of one of a bubble, a dome and a sphere.

27. The plaster according to claim 1, wherein a protective film is provided on a side facing the at least one of the damaged skin, the mucous membrane and the open wound, which is removed before use.

28. The plaster according to claim 1, wherein one of a film and a membrane, which is permeable to the medicament, is provided on a side facing the at least one of the damaged skin, the mucous membrane and the open wound.

29. The plaster according to claim 28, wherein the film and the membrane is substantially impermeable to proteolytic enzymes from the wound secretion.

30. The plaster according to claim 28 wherein the film and the membrane is made from a biodegradable material.

31. The plaster according to claim 1, wherein the support matrix including its structures in the container regions and the channel shaped regions is made from one of a polymeric plastic, a silicone or a natural elastomer.

32. The plaster according to claim 1, wherein the support matrix including its structures in the container regions and the channel shaped regions is made from a biodegradable material.

33. The plaster according to claim 1, wherein the plaster furthermore comprises a self-adhesive attachment means which completely seals off the support matrix with at least one of the active compound and the medicament and thus the at least one of the damaged skin, the mucous membrane and the open wound in at least one of an air-tight and a pressure-tight manner.

34. The plaster according to claim 1, wherein the medicament introduced into the cavities in the container regions is a polypeptide or protein.

35. The plaster according to claim 34, wherein the medicament introduced into the structures is one of a polypeptide and a protein having a molecular weight of 10-50 kD.

36. The plaster according to claim 34, wherein the one of the polypeptide and the protein is proteolysis-sensitive.

37. The plaster according to claim 34, wherein the one of the polypeptide and the protein is a growth factor or cytokine.

38. The plaster according to claim 37, wherein the one of the polypeptide and the protein is erythropoietin (EPO), a biologically active derivative or a fragment thereof.

39. The plaster according to claim 1, wherein the at least one active compound and the medicament is one of a growth factor, a cytokine which is capable of promoting specific tissue regeneration for covering the wound in one of the skin and the mucous membrane damage.

40. The plaster according to claim 1, wherein the plaster is utilized for the regenerative healing of one of the damaged skin, the mucous membrane and the open wound.

* * * * *